(12) United States Patent
Horan et al.

(10) Patent No.: US 8,911,692 B2
(45) Date of Patent: Dec. 16, 2014

(54) LIQUID ANALYZER DEVICE AND RELATED METHOD

(75) Inventors: Martin Horan, County Cork (IE); Seamus O'Mahony, County Cork (IE)

(73) Assignee: Analytical Developments Limited, County Cork (IE)

( * ) Notice: Subject to any disclaimer, the term of this patent is extended or adjusted under 35 U.S.C. 154(b) by 0 days.

(21) Appl. No.: 13/810,888

(22) PCT Filed: Jul. 19, 2011

(86) PCT No.: PCT/IE2011/000039
§ 371 (c)(1),
(2), (4) Date: Jan. 17, 2013

(87) PCT Pub. No.: WO2012/011090
PCT Pub. Date: Jan. 26, 2012

(65) Prior Publication Data
US 2013/0121876 A1    May 16, 2013

(30) Foreign Application Priority Data

Jul. 19, 2010   (IE) .................................. S2010/0449

(51) Int. Cl.
| | |
|---|---|
| B01J 10/00 | (2006.01) |
| B01F 3/04 | (2006.01) |
| B01F 11/00 | (2006.01) |
| B01F 15/02 | (2006.01) |
| B01F 5/06 | (2006.01) |
| G01N 31/00 | (2006.01) |

(52) U.S. Cl.
CPC ............ B01F 3/0446 (2013.01); G01N 31/005 (2013.01); B01F 3/04099 (2013.01); *B01F 2215/0431* (2013.01); *B01F 2215/0468* (2013.01); *B01F 2215/0409* (2013.01); *B01F 2215/0454* (2013.01); B01F 11/0074 (2013.01); B01F 15/0244 (2013.01); B01F 5/0685 (2013.01)
USPC ............ 422/606; 422/604; 422/516; 422/135

(58) Field of Classification Search
CPC ......................... B01F 11/0045; B01F 13/0018
USPC .................. 422/606, 604, 516, 135; 366/275; 417/413.1
See application file for complete search history.

(56) References Cited

U.S. PATENT DOCUMENTS

| | | | |
|---|---|---|---|
| 7,713,479 B2 | 5/2010 | Horan et al. | |
| 2007/0127309 A1* | 6/2007 | Nitta et al. | 366/114 |
| 2008/0124245 A1 | 5/2008 | Ito et al. | |

FOREIGN PATENT DOCUMENTS

WO      0054874 A1    9/2000

* cited by examiner

*Primary Examiner* — Natalia Levkovich
(74) *Attorney, Agent, or Firm* — Buskop Law Group, PC; Wendy Buskop

(57) ABSTRACT

An agitator (1) is for a liquid analysis system (3, 50). It has a chamber (5) for reception of a sample liquid. A passageway (6) from the bottom of the chamber (5) ends in an agitator chamber (7). A side wall of the agitator chamber (7) is formed by a diaphragm (8). The diaphragm (8) is connected to an electric motor (9) with an eccentric drive for reciprocating movement of the diaphragm (8). A gas inlet (10) in the opposite side of the body (2) is connected by a passageway (11) to the agitator chamber (7). The agitation chamber has a domed internal face opposed to the diaphragm, by which about 10% of the agitation chamber (7) volume is displaced by the inward movement of the diaphragm (8). Also, advantageously, there is a uniform application of displacement force within the agitation chamber (7) by virtue of the domed internal surface.

12 Claims, 4 Drawing Sheets

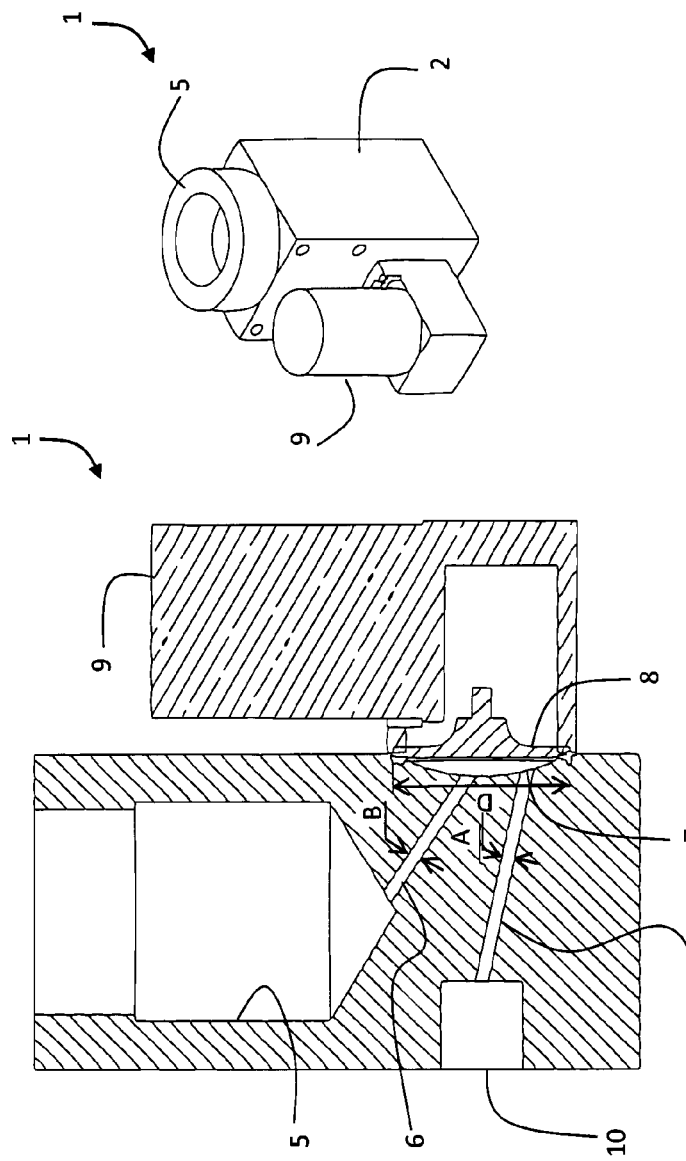
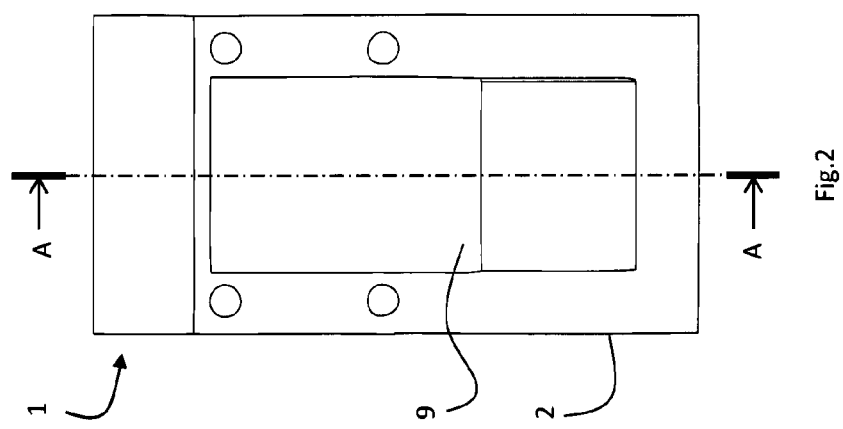

LIQUID ANALYZER DEVICE AND RELATED METHOD

FIELD OF THE INVENTION

This invention relates to an agitator for use in mixing a gas with a liquid or separating a gas from a liquid.

PRIOR ART DISCUSSION

The invention is particularly concerned with liquid analysers of the type described in US Patent Specification Nos. U.S. Pat. Nos. 7,713,479 and 7,556,773 in which ozone, an acid, a base are at different times mixed with a liquid sample in a reactor vessel. For example the liquid sample may be oxidized using a base solution and ozone. An acid may be added to the liquid sample, followed by sparging to remove carbonate. Also, a catalyst may be added to the liquid sample for reducing oxalate to carbonate.

The invention does however have more widespread use in applications where it is necessary to mix a gas with a liquid or separate a gas from the liquid.

A gas can be mixed with a liquid by simply bubbling the gas through the liquid. Where more aggressive mixing is required, usually such mixing takes place with the aid of a pump whereby the liquid and gas mixture is extracted from a chamber through a pump and circulated back to the chamber. Typically valves such as "flapper" valves are provided on the pump to control the flow of the liquid and gas mixture through the pump. However, particulate material or small fibres can block the valves thus adversely affecting the mixing of the gas and the liquid.

JP62132530, U.S. Pat. No. 5,934,885, and JP6047165 all describe arrangements for mixing of liquids. In JP62132530 membranes are used for flow control of two liquids to be mixed. U.S. Pat. No. 5,934,885 describes a multi-layered reagent pump assembly having diaphragm pumps disposed between the layers. JP6047265 describes a mixer having a vibrating diaphragm in a mixing chamber for dispersing a gas in a liquid.

The invention is directed towards providing an improved agitator for applications such as described above. One objective is to achieve efficient mixing of quantities below about 25 l while avoiding moving parts which can become blocked by particles or fibres, such as valves and pumps with rotating vanes. Another objective is to achieve improved agitation in a situation where the gas which is introduced may be quickly changed. A further objective is to avoid need for pump seals. A further objective is to allow operation in an aggressive environment.

SUMMARY OF THE INVENTION

According to the invention, there is provided an agitator for a liquid analysis system, the agitator comprising:
 a liquid sample chamber for containing a liquid,
 an agitation chamber linked by a liquid passageway (6) to the liquid sample chamber,
 a gas inlet (10) linked by a gas passageway to the agitation chamber,
 a reciprocating member mounted for contact with liquid and gas in the agitation chamber, and
 a drive means for reciprocating the reciprocating member with a displacement force to mix incoming gas and liquid in the agitation chamber and push the mixture to the liquid sample chamber.

In one embodiment, the liquid passageway (6) extends downwardly from the liquid chamber to the agitating chamber (7).

In one embodiment, the reciprocating member is a flexible diaphragm.

In one embodiment, the diaphragm forms a side wall of the agitation chamber.

In one embodiment, the diaphragm is mounted on a side of the agitation chamber opposed to the gas passageway.

In one embodiment, the diaphragm is mounted on a side of the agitation chamber opposed to the liquid passageway.

In another embodiment, the agitation chamber has a domed internal face opposed to the diaphragm.

In one embodiment, the domed internal surface includes openings to the gas passageway and to the liquid passageway.

In one embodiment, the liquid chamber, the passageways and the agitation chamber are formed in a block (2) of material.

In one embodiment, the capacity of the liquid chamber is in the range of 1 ml to 25 l.

In one embodiment, the diameter of the liquid passageway is in the range of 0.5 mm to 50 mm, and its length is in the range of 1 mm to 1 m.

In one embodiment, the diameter of the gas passageway is in the range of 0.5 mm to 50 mm.

In one embodiment, the capacity of the agitation chamber is in the range of 0.1 ml to 2 l.

In one embodiment, the frequency of the reciprocating member is in the range of 10 Hz to 1000 Hz.

In one embodiment, the agitator dimensions satisfy the ratio range of:

$$\frac{1}{14} \leq \frac{ChannelSize[B]}{DiaphragmDiameter[D]} \leq \frac{4}{14}$$

where "B" is diameter of the liquid passageway and "D" is the diameter of the reciprocating member.

In one embodiment, the agitator dimensions satisfy the ratio range of:

$$\frac{1}{35} \leq \frac{Stroke}{DiaphragmDiameter[D]} \leq \frac{3}{56}$$

where "Stroke" is the stroke of the reciprocating member and "D" is the diameter of the reciprocating member.

In one embodiment, the agitator dimensions satisfy the ratio range of:

$$\frac{1}{14} \leq \frac{InletChannelSize[A]}{DiaphragmDiameter[D]} \leq \frac{4}{14}$$

where "A" is the diameter of the gas passageway and "D" is the diameter of the reciprocating member.

In another aspect, the invention provides a liquid analyser comprising an agitator, a gas supply, a liquid supply for a base or an acid solution, and an analyzer component for analysis of gas drawn from above liquid or of liquid in the analyzer, wherein the agitator comprises:
 a liquid sample chamber for containing a liquid,
 an agitation chamber linked by a liquid passageway to the liquid sample chamber,
 a gas inlet linked by a gas passageway to the agitation chamber, a reciprocating member mounted for contact with liquid and gas in the agitation chamber, and a drive means for reciprocating the reciprocating member with a displacement force to mix incoming gas and liquid in the agitation chamber and push the mixture to the liquid sample chamber.

In one embodiment, the gas supply is adapted to deliver a gas under a pressure sufficient for continuous delivery of a gas to the agitation chamber and against the action of the reciprocating member.

In a further aspect, the invention provides an analysis method performed by an agitator as defined above in any embodiment, the method including drawing liquid from the sample liquid chamber through the liquid passageway passageway, adding gas to the liquid in the agitation chamber and an end of the liquid passageway and then forcing the liquid and gas through the liquid passageway into the sample liquid chamber.

In one embodiment, the gas is supplied to the agitation chamber with a continuous flow during analysis.

In one embodiment, the liquid chamber is filled and emptied via the liquid passageway, the agitation chamber, and the gas passageway.

In various other embodiments the invention provides an agitator for mixing a gas with a liquid or separating a gas from a liquid has a chamber for reception of the liquid, and a reciprocating member connected to the chamber, and drive means for reciprocating the reciprocating member.

In preferred embodiments a passageway communicates between the chamber and an agitating chamber within which the reciprocating member is mounted. A gas inlet line is connected to the passageway for delivery of gas through the passageway into the chamber. Preferably the gas inlet line connects to the agitating chamber. The reciprocating member is a flexible diaphragm.

In another aspect the invention provides a liquid analyser incorporating the agitator.

In a further aspect there is provided a method of mixing a gas with a liquid, including drawing liquid from a chamber through a passageway, adding gas to the liquid in the passageway and then forcing the liquid and gas through the passageway into the chamber.

DETAILED DESCRIPTION OF THE INVENTION

Brief Description of the Drawings

The invention will be more clearly understood from the following description of some embodiments thereof, given by way of example only with reference to the accompanying drawings in which:

FIG. 2 is a front view of an agitator of the system of FIG. 1 with a cap omitted, FIG. 3 is a cross-sectional side view, and FIG. 4 is a perspective view of the agitator;

DESCRIPTION OF THE EMBODIMENTS

Figure 1:
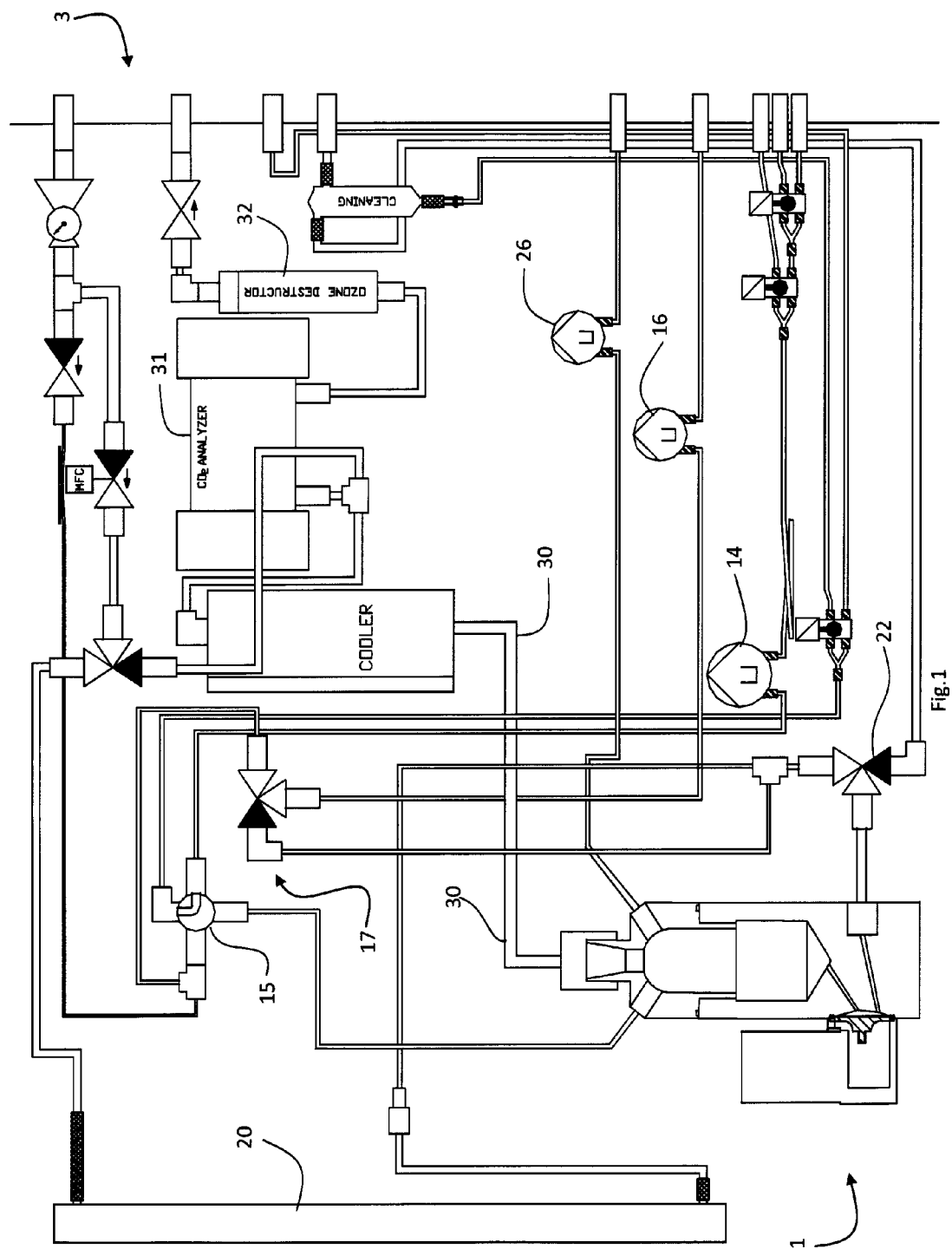
FIG. 1 is a schematic illustration of a liquid analyser of the invention.
Figure 7:
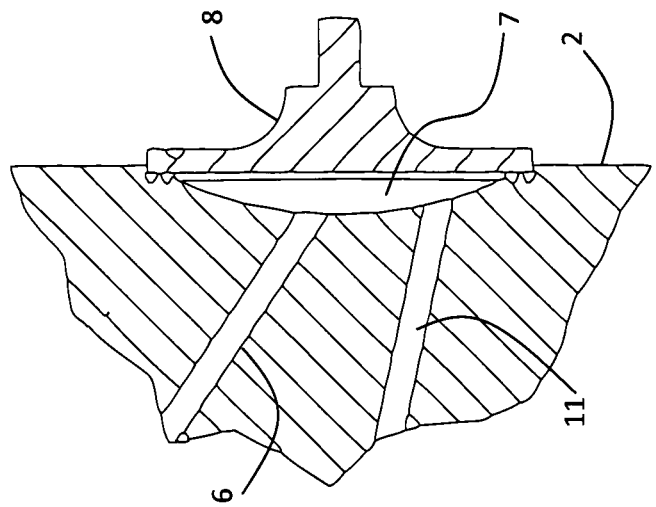
FIG. 7 is a more detailed cross-sectional view showing an agitation chamber.
Figure 6:
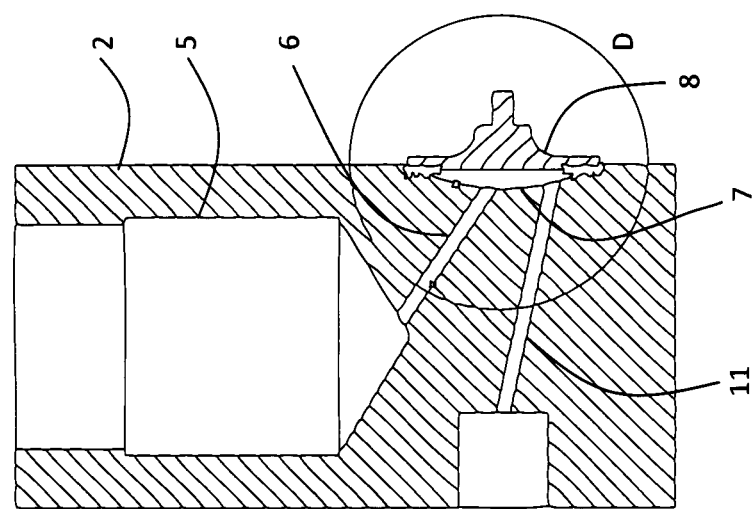
FIG. 6 is a corresponding cross-sectional view with the motor removed.
Figure 5:
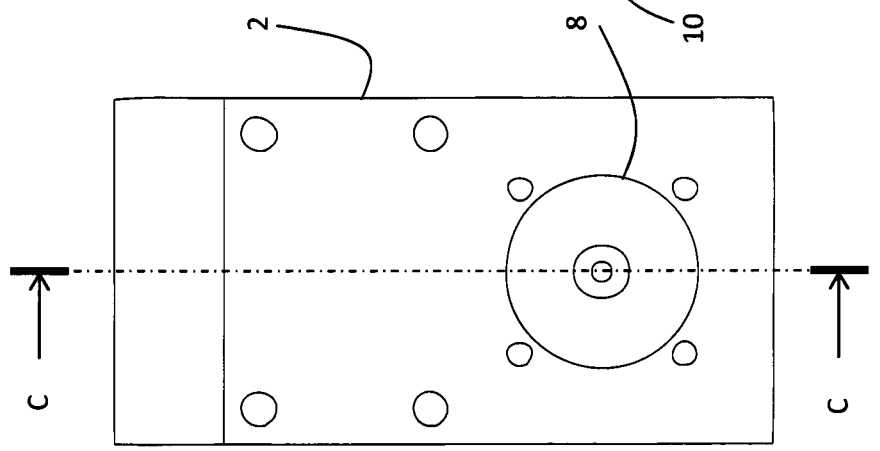
FIG. 5 is a front view of the agitator with a motor removed, to show a diaphragm more clearly.

FIG. 1 shows an agitator 1 incorporated in a liquid analyser 3. The liquid analyser 3 is at a general level similar to that disclosed in U.S. Pat. No. 7,713,479. A sample pump 14 is operable to deliver a sample liquid through a sampling valve 15 into the agitator 1. An acid pump 16 is operable to deliver acid through a 3-way valve 17 and the sampling valve 15 to the agitator 1. An ozone generator 20 is operable to deliver ozone through a second 3-way valve 22 and a gas inlet line to the agitator 1 of the reactor vessel 2. A base pump 26 connects to the agitator 1 for delivery of a base liquid to a liquid sample chamber of the agitator 1 as required. A gas outlet pipe 30 connects from the agitator 1 through a carbon dioxide analyser 31 and ozone destructor 32 to exhaust.

While the liquid analyser 3 operates, at a general level, in similar fashion to the liquid analysers described in U.S. Pat. No. 7,713,479, in this case however the sample liquid is not drawn out of a reactor chamber through a pump and then returned.

Referring to FIGS. 2 to 7, the agitator 1 has a main body 2 within which there is a chamber 5 for reception of a sample liquid. The chamber 5 is in use covered by a cap or cover, shown in FIG. 1. A passageway 6 from the bottom of the chamber 5 ends in an agitator chamber 7. A side wall of the agitator chamber 7 is formed by a diaphragm 8. The diaphragm 8 is connected to an electric motor 9 with an eccentric drive (not shown) for reciprocating movement of the diaphragm 8. A gas inlet 10 in the opposite side of the body 2 is connected by a passageway 11 to the agitator chamber 7. The agitation chamber has a domed internal face opposed to the diaphragm, by which a portion of the agitation chamber 7 volume is displaced by the inward movement of the diaphragm 8. The displaced volume may be in the range of about 10% to close to 100%. Also, advantageously, there is a uniform application of displacement force within the agitation chamber 7 by virtue of the domed internal surface.

In this embodiment, the following are the parameters of the agitator 1:

Capacity of the liquid chamber 5, 30 ml, preferably between more generally in the range of about 1 ml to about 25 l.

Diameter of the passageway 6, 3.0 mm, more generally in the range of about 0.5 mm to about 50 mm. Length of this passageway, 20 mm, more generally in the range of about 1 mm to about 1 m.

Diameter of the passageway 11, 3.0 mm, more generally in the range of about 0.5 mm to about 50 mm. Length of this passage way, 30 mm, more generally at least about 1 mm.

Capacity of the agitation chamber 7 when the diaphragm 8 is in the neutral position (vertical as viewed in FIG. 3), 20 ml, more generally in the range of 0.1 ml to about 2 l.

Diameter of the diaphragm 8, 28 mm, more generally in the range of about 1 mm to about 250 mm.

Vibration frequency of the diaphragm, 50 Hz, more generally in the range of 10 Hz to 1000 Hz.

Preferred ratios between parameters may be expressed as follows, with reference to the letters A, B, D in FIG. 3:

$$\frac{GasFlow}{DiaphragmPumpingRate} \leq 1$$

$$\frac{1}{14} \leq \frac{ChannelSize[B]}{DiaphragmDiameter[D]} \leq \frac{4}{14}$$

$$\frac{1}{35} \leq \frac{Stroke}{DiaphragmDiameter[D]} \leq \frac{3}{56}$$

$$\frac{1}{14} \leq \frac{InletChannelSize[A]}{DiaphragmDiameter[D]} \leq \frac{4}{14}$$

In general it is preferred that the stroke of the diaphragm displaces at least 25% of the agitation chamber volume, and more preferably greater than 50%.

In various examples of operation of the agitator 1 in the system 3, a sample under analysis is introduced into the chamber 5. An acid which can optionally contain a catalyst, for example manganese, is first added to acidify the liquid. This liquid is sparged by introducing a carrier gas such as oxygen through the gas inlet line 10, and optionally running the reciprocating diaphragm 8, to release any inorganic carbon from the liquid.

A basic liquid may then be introduced along with ozone, and the reciprocating diaphragm 8 effectively mixes the ozone, basic solution and sample liquid together, in an efficient manner creating hydroxyl radicals and providing optimum conditions for oxidation of the sample liquid.

An acid may be introduced, which can optionally contain a catalyst, for example manganese, and this acidifies the liquid. This liquid is sparged by introducing a carrier gas through the gas inlet 10, and optionally running the reciprocating diaphragm 8, to release any organic carbon from the liquid.

The liquid can then undergo further analysis, for example for nitrogen, phosphorus, metals, or other appropriate material.

The sample liquid may be introduced into the chamber 5 via the passageway 11. For mixing a gas with the sample liquid in the chamber 5, gas is delivered through the gas inlet 10 and the passageway 6 into the chamber 5. There is a gas flow through this passageway, with a positive input pressure. This pressure is preferably in the range of 1 mBar to 10 Bar. At the same time the diaphragm 8 is reciprocated by the motor 9. On an outward stroke the diaphragm 8 draws liquid from the chamber 5 out through the passageway 6 into the agitating chamber 7. On the inward stroke the diaphragm 8 forces gas and liquid from the agitating chamber 7 through the narrowed passageway 6 back into the chamber 5 thus promoting mixing of the gas with the liquid as it is compressed in the agitating chamber 7 and forced back through the passageway 6 into the chamber 5. The agitation action in the agitation chamber 7 may be described as a "hammering" type of action on the gas as it flows into the chamber 7. There is a balance between the gas pressure in the inlet 10 and the passageway 11 and that applied by the diaphragm 8 so that there is sufficient gas flow into the agitation chamber 7 and flow of mixed liquid and gas back up the passageway 6 into the chamber 5. Because the mixing is occurring in a small agitation chamber and not in the sample liquid chamber 5, it is very effective and in a short period of time of the order of a few minutes all of the liquid in the chamber 5 will have been adequately mixed.

The effective mixing is performed without need for the liquid to pass through a pump with moving vanes or a valve such as a flapper valve. Therefore, advantageously, there is no risk of particles or fibres from becoming clogged in moving parts and hence blocking or restricting flow in any part of the agitator 1. The agitator may therefore be used in a system such as a liquid analyzer in which slurry needs to be agitated. Indeed, it is envisaged that the agitator 1 would be suitable for use with slurry including sand grains, provided the passageways are sufficiently large.

The fact that the passageway 6 extends downwardly from the liquid chamber 5 means that there is gravity feed to the agitation chamber 7, allowing simple control of agitation by merely controlling pressure of gas flow at the inlet.

It will also be appreciated that the agitator 1 avoids need for moving seals, and hence reliability is enhanced, as is ability to wash the agitator internal surfaces.

It has also been found that the agitator 1 is very efficient as a means of sparging a gas from the liquid in the chamber 5 and more generally for removing volatile gases, carbon dioxide etc. from the liquids.

In the embodiment described above the diaphragm 8 is reciprocated using the motor 9 and associated eccentric drive. However various other methods of vibrating the diaphragm 8 are possible such as a solenoid driver for example.

It will be noted that the chambers 5 and 7 and the passageways 6 and 11 are machined from a block of plastics material to form the body 2, and the diaphragm 8 and associated motor 9 are attached directly. This provides excellent durability in use, and accuracy in manufacture. The agitator may include a block of any appropriate metal, plastic, ceramic or other suitable material, to which the reciprocating diaphragm 8 is attached.

Another advantage is that the agitator may be emptied via the passageway 6, chamber 7, and the passageway 11.

The agitation chamber 7, the gas inlet line 10, and the diaphragm 8 may be arranged so that the diaphragm 8 closes off the gas inlet line 10 as it moves inwardly into the agitating chamber 7.

It is also envisaged that a reciprocating means other than a diaphragm may be used. For example it may alternatively be a piston of any suitable material. In this case there is a moving seal, but this may not in some applications be a particular disadvantage. Where a diaphragm is used, the vibration may be caused by a different drive such as an ultrasonic drive.

Figure 8:
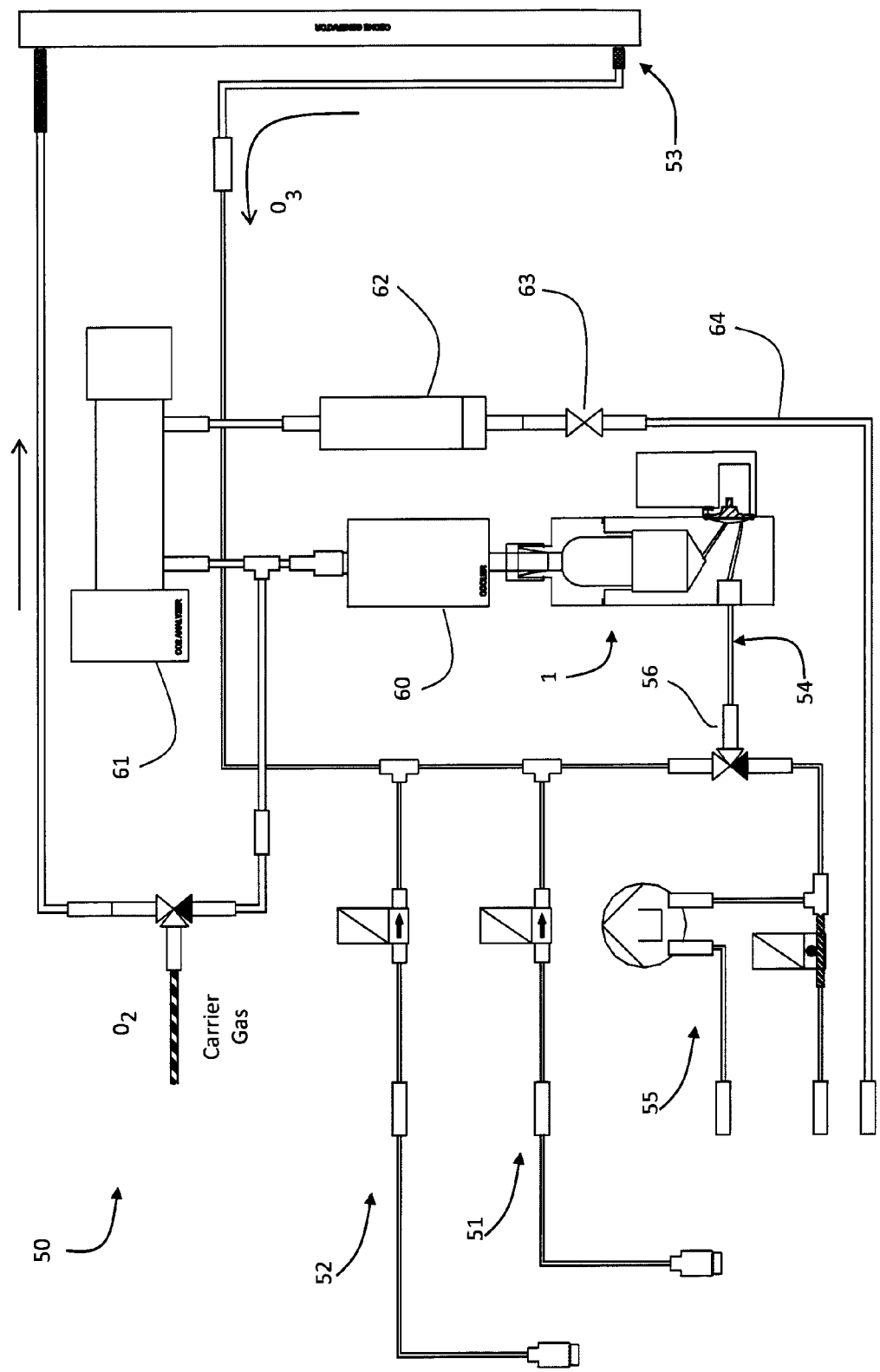
FIG. 8 is a schematic representation of an alternative liquid analyzer of the invention.

Also, an agitator if the invention may be used in any of a range of liquid analyzers. For example, as shown in FIG. 8 the agitator 1 is in a liquid analyzer 50 having a sodium hydroxide base solution supply 51, a sulphuric acid supply 52 with a catalyst, an ozone generator 53, and a gas supply 54 linked with an assembly 55 of a liquid sample supply, a drain, and an exhaust. There is also a cooler 60 and a $CO_2$ analyzer 61. As described in the prior art referenced above, ozone may pick up an acid or a base solution in different stages for delivery into the gas inlet of the agitator 1. $O_2$ is delivered as illustrated as a carrier gas and as a supply to the ozone generator 53.

Other types of liquid analyzer in which an agitator of the invention may be used include any situation where a gas stream is mixed with a liquid. Examples are any of those described in the prior art documents listed above, or COD analysis, or BOD analysis, or biological sample analysis for example to add markers to sample liquids.

The invention is not limited to the embodiments described but may be varied in construction and detail. For example the agitation chamber may be in the form of a tube, rather than being machined from a block. While the dimensions are given above on the basis of the passageways 6 and 11 being circular in cross-section, it may have any other cross-sectional shape such as rectangular or elliptical, in which case the diameter values given apply to the largest dimension in cross-section.

The invention claimed is:

1. An agitator for a liquid analysis system, the agitator comprising:
    a liquid sample chamber for containing a liquid,
    an agitation chamber linked by a liquid passageway to the liquid sample chamber,
    a gas inlet linked by a gas passageway to the agitation chamber,
    a reciprocating member mounted for contact with liquid and gas in the agitation chamber, wherein,
    the agitator further comprises a drive means connected to the reciprocating member, wherein the drive means displaces the reciprocating member to mix incoming gas from the gas inlet and liquid from the liquid sample chamber in the agitation chamber and to push the mixture back to the liquid sample chamber, via the liquid passageway, and the capacity of the liquid sample chamber is in the range of 1 ml to 25 l.

2. An agitator as claimed in claim 1, wherein the liquid sample chamber has a top opening covered by a removable cover and the liquid passageway extends downwardly from the liquid sample chamber to the agitating chamber.

3. An agitator as claimed in claim 1, wherein the reciprocating member is a diaphragm.

4. An agitator as claimed in claim 3, wherein the diaphragm forms a side wall of the agitation chamber.

5. An agitator as claimed in claim 4, wherein the diaphragm is mounted on a side of the agitation chamber opposed to the gas passageway.

6. An agitator as claimed in claim 5, wherein the diaphragm is mounted on a side of the agitation chamber opposed to the liquid passageway.

7. An agitator as claimed in claim 1, wherein the agitation chamber has a domed internal face opposed to the flexible diaphragm.

8. An agitator as claimed in claim 7, wherein the domed internal surface includes openings to the gas passageway and to the liquid passageway.

9. An agitator as claimed in claim 1, wherein the liquid sample chamber, the passageways and the agitation chamber are formed in a block of material.

10. An agitator as claimed in claim 1, wherein a diameter of the liquid passageway is in the range of 0.5 mm to 50 mm, and its length is in the range of 1 mm to 1 m, wherein a diameter of the gas passageway is in the range of 0.5 mm to 50 mm, and wherein the capacity of the agitation chamber is in the range of 0.1 ml to 2 l.

11. An agitator as claimed in claim 1, wherein the agitator dimensions satisfy the ratio range of:

$$\frac{1}{14} \leq \frac{ChannelSize[B]}{DiaphragmDiameter[D]} \leq \frac{4}{14}$$

where "ChannelSize[B]" is diameter of the liquid passageway and "DiaphragmDiameter[D]" is the diameter of the reciprocating member; and wherein the agitator dimensions satisfy the ratio range of:

$$\frac{1}{35} \leq \frac{Stroke}{DiaphragmDiameter[D]} \leq \frac{3}{56}$$

where "Stroke" is the stroke of the reciprocating member and "DiaphragmDiameter[D]" is the diameter of the reciprocating member; and wherein the agitator dimensions satisfy the ratio range of:

$$\frac{1}{14} \leq \frac{InletChannelSize[A]}{DiaphragmDiameter[D]} \leq \frac{4}{14}$$

where "InletChannelSize[A]" is the diameter of the gas passageway and "DiaphragmDiameter[D]" is the diameter of the reciprocating member.

12. A liquid analyzer comprising an agitator, a gas supply, a liquid supply for a base or an acid solution, and an analyzer component for analysis of gas drawn from above liquid or of liquid in the analyzer, wherein the agitator comprises:

a liquid sample chamber for containing a liquid, an agitation chamber linked by a liquid passageway to the liquid sample chamber, a gas inlet linked by a gas passageway to the agitation chamber, a reciprocating member mounted for contact with liquid and gas in the agitation chamber, and wherein the gas supply is adapted to deliver a gas under a pressure sufficient for continuous delivery of a gas to the agitation chamber and against the action of the reciprocating member, wherein the agitator further comprises a drive means connected to the reciprocating member, wherein the drive means displaces the reciprocating member to mix incoming gas from the gas inlet and liquid from the liquid sample chamber in the agitation chamber and to push the mixture back to the liquid sample chamber via the liquid passageway, and wherein the capacity of the liquid sample chamber is in the range of 1 ml to 25 l.

* * * * *